(12) United States Patent
Vange (10) Patent No.: US 12,070,531 B2
(45) Date of Patent: Aug. 27, 2024

(54) POLYMERIC COATINGS

(71) Applicant: Coloplast A/S, Humlebaek (DK)

(72) Inventor: Jakob Vange, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 630 days.

(21) Appl. No.: 16/639,130

(22) PCT Filed: Aug. 16, 2018

(86) PCT No.: PCT/DK2018/050199
§ 371 (c)(1),
(2) Date: Feb. 14, 2020

(87) PCT Pub. No.: WO2019/034222
PCT Pub. Date: Feb. 21, 2019

(65) Prior Publication Data
US 2020/0206389 A1 Jul. 2, 2020

(30) Foreign Application Priority Data
Aug. 17, 2017 (DK) .......................... PA 2017 70623

(51) Int. Cl.
| | | |
|---|---|---|
| *A61L 29/08* | (2006.01) | |
| *A61L 29/04* | (2006.01) | |
| *A61L 29/16* | (2006.01) | |
| *C09D 133/02* | (2006.01) | |
| *A61M 25/00* | (2006.01) | |

(52) U.S. Cl.
CPC .......... *A61L 29/085* (2013.01); *A61L 29/041* (2013.01); *A61L 29/16* (2013.01); *C09D 133/02* (2013.01); *A61L 2300/404* (2013.01); *A61L 2300/608* (2013.01); *A61L 2400/10* (2013.01); *A61L 2420/02* (2013.01); *A61L 2420/08* (2013.01); *A61M 25/0017* (2013.01); *A61M 25/002* (2013.01)

(58) Field of Classification Search
None
See application file for complete search history.

(56) References Cited

U.S. PATENT DOCUMENTS

| | | | |
|---|---|---|---|
| 828,789 A | 8/1906 | Wagner | |
| 5,202,483 A | 4/1993 | Rehmer et al. | |
| 5,278,200 A | 1/1994 | Coury et al. | |
| 5,506,279 A * | 4/1996 | Babu ..................... | C07C 233/52 |
| | | | 522/904 |
| 6,245,922 B1 * | 6/2001 | Heilmann ................. | C08F 2/50 |
| | | | 552/208 |
| 2005/0065232 A1* | 3/2005 | Okimoto ................ | A01K 75/00 |
| | | | 523/122 |

FOREIGN PATENT DOCUMENTS

| | | | |
|---|---|---|---|
| CN | 103951576 A | * | 7/2014 |
| EP | 0445641 B1 | | 1/1994 |
| EP | 2303346 B1 | | 9/2013 |
| GB | 1534320 A | | 11/1978 |
| JP | 2016216635 A | | 12/2016 |
| WO | WO1995010552 A1 | | 4/1995 |
| WO | 0068218 A1 | | 11/2000 |
| WO | 03055611 A1 | | 7/2003 |
| WO | 2006120212 A1 | | 11/2006 |
| WO | WO2007065721 A2 | | 6/2007 |
| WO | 2011163327 A2 | | 12/2011 |
| WO | 2013029621 A1 | | 3/2013 |
| WO | 2015061097 A1 | | 4/2015 |
| WO | 2017173114 A1 | | 10/2017 |

OTHER PUBLICATIONS

Czech et al. Reviews on Advanced Materials Science 2007 14:141-150 (Year: 2007).*

* cited by examiner

*Primary Examiner* — Melissa S Mercier
*Assistant Examiner* — Caralynne E Helm
(74) *Attorney, Agent, or Firm* — Coloplast Corp., Coloplast A/S; Nick Baumann (57) ABSTRACT

Coatings for medical devices, e.g. urinary catheters, are provided, which comprise photoinitiator monomers with acrylamide photoinitiator functionality.

12 Claims, 2 Drawing Sheets

POLYMERIC COATINGS

SUMMARY

Coatings for medical devices, e.g. urinary catheters, are provided, which comprise photoinitiator monomers with acrylamide photoinitiator functionality.

BACKGROUND

Curing via ultraviolet (UV) radiation requires efficient methods of initiating the chemical reaction responsible for the curing process. Photoinitiators convert radiation into chemical energy, and are employed in many cases to promote curing of various materials.

Intermittent urinary catheters should be lubricious (i.e. with low coefficient of friction), so that they can readily be inserted into and removed from the urinary tract. To this end, such catheters are provided with wet, lubricious (e.g. hydrophilic) polymeric coatings which have low coefficient of friction properties.

Additionally, polymeric coatings on urinary catheters should be readily attached to the underlying surface, so that coating is simplified, and physical degradation of the coating during use is reduced.

SUMMARY

Despite previous efforts, there remains a need for novel polymeric coatings which can be easily formed on an underlying surface, and which are chemically and physically stable, especially in acidic environments. The polymeric coatings should provide bacteria repellence while maintaining or improving the lubricous properties.

The inventors have realised that acidic polymer coatings provide useful properties, e.g. lubricity and bacteria repellence. However, they have also discovered that properties such as lubricity (low friction) can depend heavily on the particular pKa of the polymer moieties, and the pH at which they are used. The present technology aims to provide acidic polymer coatings, and methods for their formation in which good lubricity and bacterial repellency can be maintained, even at low pH values.

In a first aspect, therefore, a polymeric coating for a urinary catheter is provided, being a copolymer of at least a first photoinitiator monomer and at least one second monomer;
said first monomer having formula (I):

(I)

in which:
Pi is a photoinitiator moiety;
Z is a linker moiety selected from a single bond, optionally substituted $C_1$-$C_{12}$ alkylene, optionally substituted $C_1$-$C_{12}$ alkenylene; —O—; —S—; —$NR^a$—; —CO—$NR^a$—; optionally substituted heterocyclyl; optionally substituted arylene; optionally substituted —[O—($C_1$-$C_{12}$ alkylene)]$_n$—, optionally substituted —[NHR$^1$—($C_1$-$C_{12}$ alkylene)]$_n$; optionally substituted —[S—($C_1$-$C_{12}$ alkylene)]$_n$—; and combinations thereof; wherein n is an integer from 1-20, and wherein $R^a$ is H or optionally substituted $C_1$-$C_6$ alkyl;
$R^1$ is selected from H or optionally substituted $C_1$-$C_6$ alkyl;
$R^2$ is selected from H or optionally substituted $C_1$-$C_6$ alkyl;
wherein $R^2$ or a part thereof may be linked to Z to form one or more ring structures;
and wherein said at least one second monomer comprises an unsaturated C=C bond.

A method for synthesising such a polymeric coating is also provided, said method comprising the step of co-polymerizing a first monomer of formula (I) with at least one second monomer comprising an unsaturated C=C bond.

A method for coating a urinary catheter is also provided, said method comprising the steps of:
a. applying the polymeric coating as defined above to an outer surface of said urinary catheter and
b. irradiating said polymer coating so as to fix the polymeric coating to said outer surface.

A further aspect concerns the use of the polymeric coating as above, for providing bacteria repellency to a surface of a urinary catheter.

In a further aspect, an intermittent urinary catheter is provided, which is coated with the polymeric coating according to the above.

In yet a further aspect, a kit is provided comprising the intermittent catheter set out herein, and a catheter package, wherein said intermittent catheter is sealed within said catheter package, and wherein a swelling liquid is also present within said catheter package and in contact with said intermittent catheter, wherein said swelling liquid has a pH of 5 or less, such as 3 or less.

Further aspects of the invention are presented in the following description and dependent claims.

DETAILED DISCLOSURE

Definitions

In the following, when a part of a molecule is described as "optionally substituted" it is meant that said part may be substituted by one or more substituents selected from: $C_1$-$C_6$ linear, branched or cyclic alkyl, aryl, —OH, —CN, halogens, amines, amides, alcohols, ethers, thioethers, sulfones and derivatives thereof, sulfoxides and derivatives thereof, carbonates, isocyanates, nitrates and acrylates. Notably, when Z is $C_1$-$C_{12}$ alkylene substituted with a $C_1$-$C_6$ alkyl substituent, said $C_1$-$C_6$ alkyl substituent may form one or more rings with the photoinitiator moiety Pi.

The term "heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "alkylene" is used in the following to specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched, linear and cyclic alkylenes, with branched alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "alkenylene" is used in the following to specify moieties derived from alkenes in which two H atoms have been removed to form a diradical species. Examples include ethyenylene —$CH_2$=$CH_2$— and propenylene —$C_3H_4$— moieties. The term "alkenylene" includes branched, linear and cyclic alkenylene, with linear alkenylene being most preferred.

The terms "aryl" or "arylene" are used to define an unsaturated cyclic system which contains a delocalised π-electron system about the ring. Aryl or arylene groups may comprise from 4-12 atoms, suitably from 6-8 atoms, most suitably 6 atoms. "Aryl" is preferably phenyl (—$C_6H_5$). Arylene is used to define a disubstituted aryl moiety, and is preferably phenylene.

The terms "aryl" or "arylene" is also used to include unsaturated heterocycles—rings in which one or more atoms in the ring (e.g. 1-3 atoms) are N, S, P or O. Such heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings).

The term "aryl" also includes fused ring systems and biaryl (particularly biphenyl) systems.

Curing

Curing is primarily initiated by exposing the substances to high energy irradiation, preferably UV light. The photoinitiated process takes place by methods which are known per se, through irradiation with light or UV irradiation in the wavelength range from 100 to 500 nm. Irradiation sources which may be used are sunlight or artificial lamps or lasers. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelengths. In particular, scattering phenomena are less pronounced at longer wavelength, thus giving a larger penetration depth in the material. Thus, photoinitiators which absorb, and can induce curing, at longer wavelength are of interest. By judiciously choosing substituents on the photoinitiator moieties, the absorption spectrum of the photoinitiator can to some extent be red-shifted, which would then facilitate curing at comparatively greater depths.

Polymeric Coating

A polymeric coating for a urinary catheter is provided. The polymeric coating is a copolymer of a first photoinitiator monomer and at least one second monomer.

Suitably, the content of first photoinitiator monomer in said polymeric coating is between 0.1-5 mol %, more suitably between 0.5-5 mol %.

First Monomer-Photoinitiator

One component of the polymeric coating is a first photoinitiator monomer having the general formula (I):

(I)

in which Pi is a photoinitiator moiety;
Z is a linker moiety selected from a single bond, optionally substituted $C_1$-$C_{12}$ alkylene, optionally substituted $C_1$-$C_{12}$ alkenylene; —O—; —S—; —$NR^a$—; —CO—$NR^a$—; optionally substituted heterocyclyl; optionally substituted arylene; optionally substituted —[O—($C_1$-$C_{12}$ alkylene)]$_n$—, optionally substituted —[$NHR^1$—($C_1$-$C_{12}$ alkylene)]$_n$; optionally substituted —[S—($C_1$-$C_{12}$ alkylene)]$_n$—; and combinations thereof; wherein n is an integer from 1-20, and wherein $R^a$ is H or optionally substituted $C_1$-$C_6$ alkyl;
$R^1$ is selected from H or optionally substituted $C_1$-$C_6$ alkyl;
$R^2$ is selected from H or optionally substituted $C_1$-$C_6$ alkyl;
wherein $R^2$ or a part thereof may be linked to Z to form one or more ring structures.

A photoinitiator is defined as a substance (other than a reactant) which, on absorption of light, generates reactive species (ions or radicals) and initiates one or several chemical reactions or transformation. One preferred property of the photoinitiator is good overlap between the UV light source spectrum and the photoinitiator absorption spectrum. Another desired property is a minor or no overlap between the photoinitiator absorption spectrum and the intrinsic combined absorption spectrum of the other components in the matrix. Good compatibility of the photoinitiator in the matrix of material to be cured is also a property of interest.

The photoinitiator monomers with the general formula I comprise a photoinitiator moiety, Pi, which provides the photoinitiator monomers with the required response to UV radiation.

The photoinitiator moieties are efficient in transforming light from the UV or visible light source to reactive radicals which can abstract hydrogen atoms and other labile atoms from other molecules.

Radical photoinitiator moieties can be classified as either cleavable (Norrish type I reaction) or non-cleavable. Upon excitation, Norrish Type-I photoinitiator moieties spontaneously break down into two radicals. In one aspect, the photoinitiator moiety is a Norrish Type-I photoinitiator moiety.

Photoinitiator moieties (Pi) in Formula (I) may be selected from, but not exclusively restricted to, the group consisting of: benzoin ethers, 1-phenyl-2-hydroxy-2-alkyl ketones, 1-phenyl-2-amino-2-alkyl ketones, benzophenones, thioxanthones, xanthones, acridones, anthraquinones, fluorenones, dibenzosuberones, benzils, benzil ketals, acetophenones, α-alkoxy-acetophenones, α,α-dialkoxy-acetophenones, α-hydroxy-α-alkyl-phenones, α-hydroxy-α, α-dialkyl-phenones, alkyl phenylglyoxylates, camphorquinones, acyl-phosphine oxides, and phenyl ketocoumarins.

Of these, preferred photoinitiator moieties are selected from acetophenones, α-alkoxy-acetophenones, α,α-dialkoxy-acetophenones, α-hydroxy-α-alkyl-phenones, α-hydroxy-α, α-dialkyl-phenones and alkyl phenylglyoxylates.

In particular, Pi may be a Norrish Type-I photoinitiator moiety having the general formula (V):

—(Ph)—(X)$_m$  (V)

wherein Ph is an optionally-substituted phenyl ring;
wherein m is an integer of 1-5, such that m X moieties may be present at any position on Ph;
and wherein X is selected from in which R is selected from H or optionally substituted $C_1$-$C_6$ alkyl.

In general formula (V), X is suitably present at the para-position on Ph. Suitably, m is 1 or 2, preferably 1.

Linker, Z

The portion of the photoinitiator monomer of Formula (I) indicated by Z is a linker. Linker Z therefore has two ends. At one end, therefore, Z is joined to the photoinitiator moiety Pi; at the other end, Z is joined to an acrylamide functionality.

The size of the linker Z is selected according to the desired properties of the photoinitiator. Suitably, the linker Z has a molecular weight of less than 10000 Da, suitably less than 5000 Da, most suitably less than 1000 Da. The linker Z preferably comprises no more than 50 atoms, preferably no more than 30 atoms.

In the photoinitiators of Formula (I) above, Z is a linker moiety. Z is selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$—, optionally substituted —[NHR$^1$—($C_1$-$C_{12}$ alkylene)]$_n$; optionally substituted —[S—($C_1$-$C_{12}$ alkylene)]$_n$—; and combinations thereof; wherein n is an integer from 1-20, and wherein R$^a$ is H or optionally substituted $C_1$-$C_6$ alkyl. The definition of Z excludes ester moieties, which may be susceptible to cleavage under certain conditions.

Suitably, n is an integer from 1-10, more suitably from 1-5, such as e.g. 1, 2, 3, 4 or 5.

In particular embodiments, linker Z may have the structure:

—C(R$^3$)(R$^4$)—Za— in which the —C(R$^3$)(R$^4$)— moiety is linked to the acrylamide N-atom in formula (I);

wherein Za is a linker moiety selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$—, optionally substituted —[NHR$^1$—($C_1$-$C_{12}$ alkylene)]$_n$; optionally substituted —[S—($C_1$-$C_{12}$ alkylene)]$_n$—; and combinations thereof; wherein n is an integer from 1-20, and wherein R$^a$ is H or optionally substituted $C_1$-$C_6$ alkyl;

R$^3$ and R$^4$ are independently selected from H or optionally substituted $C_1$-$C_6$ alkyl; wherein R$^3$ or R$^4$, or a part thereof, may be linked to Za to form one or more ring structures. R$^3$ and R$^4$ may independently be selected from optionally substituted $C_1$-$C_6$ alkyl, such as $C_1$-$C_6$ alkyl, e.g. methyl, ethyl or propyl, preferably methyl. In aspects, R$^3$ and R$^4$ are the same.

Figure 1A:
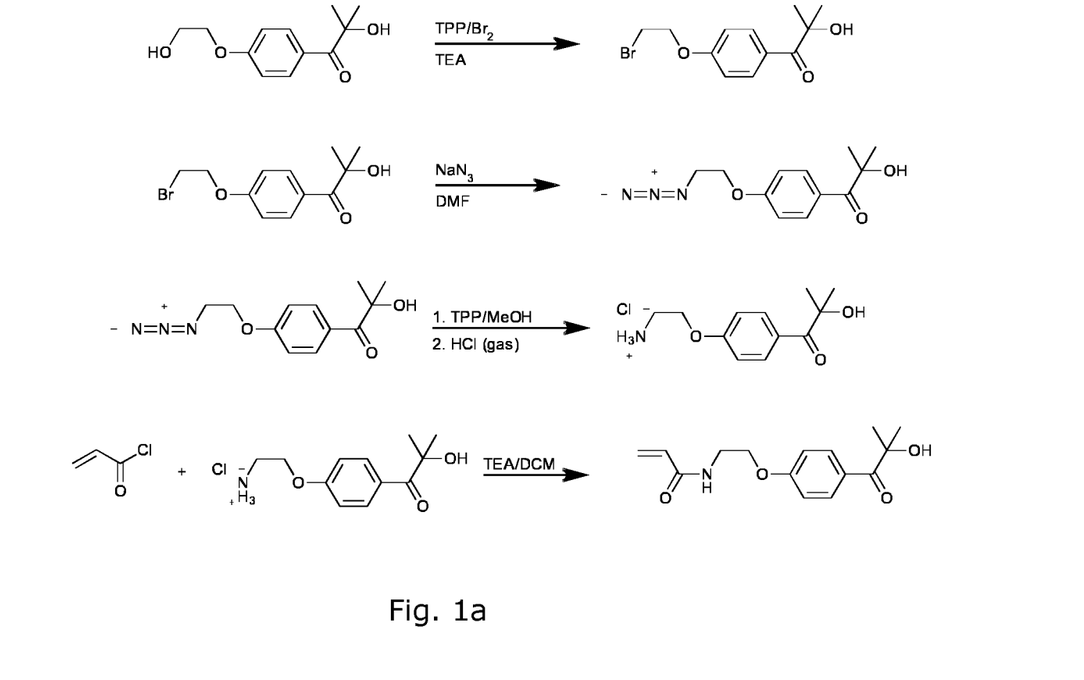
FIGS. 1a-1c show possible synthetic routes to photoinitiators of general formula (I).
Figure 1B:
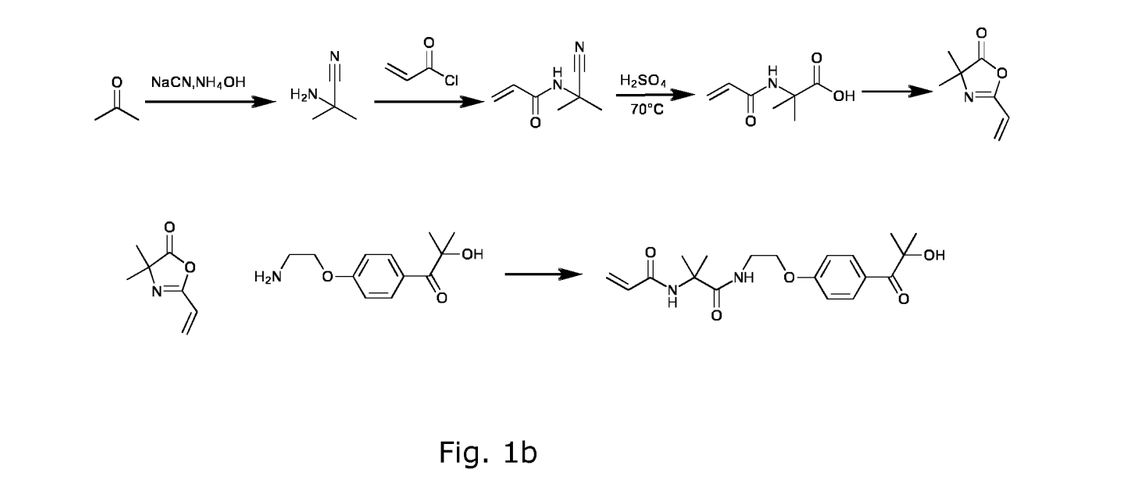
Figure 1C:
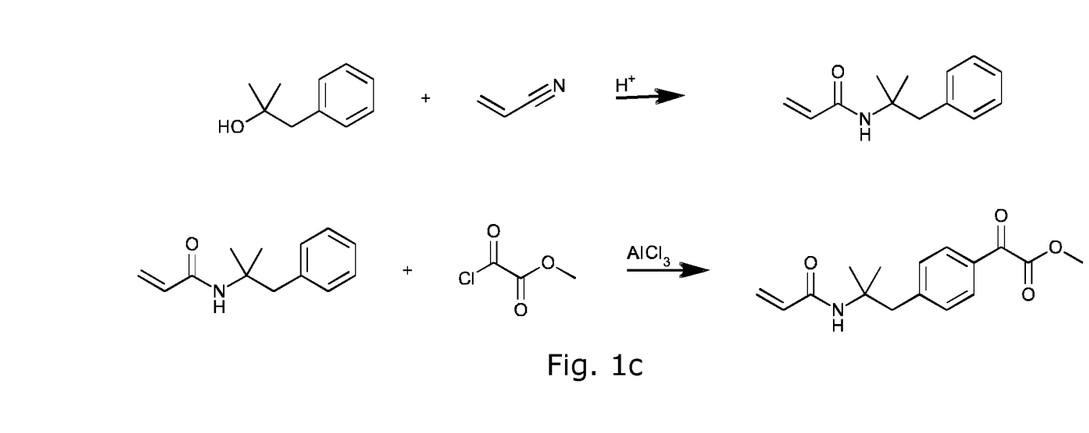

Photoinitiators with such linkers may be advantageously synthesised via the Ritter reaction (cf. FIG. 1c). Advantageously, for the Ritter reaction, R$^3$ and R$^4$ are not hydrogen.

In that Z may comprise a combination of the above-mentioned groups, the technology encompasses photoinitiators in which Z is made up of two or more of the above-mentioned groups in series. In all of the above, the —($C_1$-$C_{12}$ alkylene)— and -aryl- groups may be substituted or unsubstituted. Other chemically-feasible structures for Z can be determined by the person skilled in the art.

Suitably, Z is selected from a single bond, $C_1$-$C_{12}$ alkylene, $C_1$-$C_{12}$ alkenylene; —O—; —S—; —NR$^a$—; or —[O—($C_1$-$C_{12}$ alkylene)]$_n$—, wherein R$^a$ is H or optionally substituted $C_1$-$C_{12}$ alkyl and n is an integer from 1-20. In aspects, Z is selected from a single bond, $C_1$-$C_{12}$ alkylene or —O—($C_1$-$C_{12}$ alkylene)—, such as $C_1$-$C_6$ alkylene or —O—($C_1$-$C_6$ alkylene)—.

Similarly, Za may be selected from a single bond, $C_1$-$C_{12}$ alkylene, $C_1$-$C_{12}$ alkenylene; —O—; —S—; —NR$^a$—; or —[O—($C_1$-$C_{12}$ alkylene)]$_n$—, wherein R$^a$ is H or optionally substituted $C_1$-$C_{12}$ alkyl and n is an integer from 1-20. In aspects, Za is selected from a single bond, $C_1$-$C_{12}$ alkylene or —O—($C_1$-$C_{12}$ alkylene)—, such as $C_1$-$C_6$ alkylene or —O—($C_1$-$C_6$ alkylene)—.

Photoinitiators of Formula (I) in which Z comprises an electron-donating group adjacent to Pi are advantageous, as this provides opportunities to tailor the UV absorption of the photoinitiator moiety.

Other Substituents

In the photoinitiators of general formula (I), R$^1$ is suitably H or methyl. R$^1$ may also be optionally substituted $C_1$-$C_6$ alkyl, such as e.g. methyl, ethyl, propyl, butyl, pentyl or hexyl. R$^1$ may be straight-chain, branched or cyclic alkyl.

R$^2$ is selected from H or optionally substituted $C_1$-$C_6$ alkyl; wherein R$^2$ or a part thereof may be linked to Z to form one or more ring structures. R$^2$ is suitably H.

Further Photoinitiator Structures

A sub-structure which describes photoinitiator monomers of Formula I has the general formula (Ia):

(Ia)

wherein R$^1$, R$^2$, R$^3$, Z, Ph, X, and m are as defined above.

Another sub-structure which describes photoinitiator monomers of Formula (I), has the general formula (Ib):

(Ib)

Wherein Za is a linker moiety selected from a single bond, —$C_1$-$C_6$ alkylene— or —O—($C_1$-$C_6$ alkylene)—; $R^1$ and $R^2$ are as defined above; $R^3$ and $R^4$ are independently selected from H or methyl; X is selected from

In all sub-structures Ia-Ib, suitable options for Z, R, $R^1$ and $R^2$ are as set out above.

Suitable photoinitiator monomers include:

Photoinitiator monomers of particular interest are

Second Monomer

The polymeric coating further comprises at least one second monomer. The second monomer(s) comprise an unsaturated C=C bond, and are therefore able to co-polymerise with the first photoinitiator monomers described above. The second monomer suitably comprises an acryloyl moiety (C=C—C=O). The second monomer may be selected from acrylic acid, an acrylamide or an acrylic acid ester, or mixtures thereof. Particular monomers which may be used are acrylic acid, C1-C6 acrylic esters such as methyl acrylate or ethyl acrylate, 2-acrylamido-2-methylpropane sulfonic acid, 2-acrylamido-2-methylpropane sulfonic acid sodium salt, 4-acryloyl-morpholine, hydroxyethyl methacrylate, acrylamide, N,N-dimethyl-acrylamide, methyl vinyl ether and ethyl vinyl ether.

Suitably, the polymeric coating comprises two second monomers, which are copolymerised together with the first photoinitiator monomer. In a particular aspect, the two second monomers are acrylic acid and sodium 2-acrylamido-2-methylpropane sulfonic acid (Na-AMPS).

Polymeric Coating Synthesis

A method for synthesizing a polymeric coating as described herein is also provided. The method comprises the step of co-polymerizing a first monomer of formula (I) with at least one second monomer comprising an unsaturated C=C bond.

Further details of the coating synthesis are described in the experimental section.

Coating

In one embodiment, a method for coating a urinary catheter is provided. Said method comprises the steps of:
a. applying the polymeric coating described herein to an outer surface of said urinary catheter and
b. irradiating said polymeric coating so as to fix the polymeric coating to said outer surface.

In this manner, the polymeric coating is grafted to the outer surface of the urinary catheter in an easy manner. Further details of the coating method are described in the experimental section.

Additional Components

For the purposes of coating, the polymeric coating may additionally comprise a plasticiser. A plasticizer will improve the physical properties of the coating, and will reduce the tendency of the coatings to detach from the substrate when dried. Suitable plasticizers include PEG, 1,2-propylene carbonate, propylene glycol, ethylene carbonate, glycerol, sorbitol, citrofol A1, citrofol A2, monoacetin, diacetin and triacetin.

The choice of plasticizer is dependent on the polymer composition. When the polymer coating contains acrylic acid, PEG is a suitable plasticizer. Poly(Na-AMPS) can be plasticized with glycerol, and poly(ACMO) can be plasticized with 1,2-propylene carbonate.

In certain circumstances, e. g. PEG, the plasticiser may be incorporated into the polymeric coating during UV irradiation of the polymeric coating.

In other circumstances, e.g. glycerol and propylene carbonate, the plasticiser may be present in admixture with the polymeric coating.

Suitable solvents for use in the synthesis, formulation and coating of the polymeric coating are alcohols (e.g. methanol, ethanol, 1-propanol, 2-propanol) and water, and combinations thereof.

It is possible to graft the photoinitiator-functional polymeric coatings provided herein onto a substrate, such as a polyurethane substrate, when using a suitable primer on the substrate. Therefore, in one aspect, said urinary catheter comprises a substrate material and a primer layer, and wherein the primer layer constitutes the outer surface of the urinary catheter. In a further aspect, said primer layer is a layer of photoinitiator (e.g. a polymeric multifunctional photoinitiator) and optionally an acrylate monomer or a multifunctional acrylate monomer.

Further Aspects

Also provided is the use of the polymeric coating as described herein for providing bacteria repellency to a surface of a urinary catheter.

Also provided is an intermittent urinary catheter coated with the polymeric coating described herein. The intermittent catheter is suitably wet-stored and ready-to-use.

The intermittent urinary catheters described herein can provide both a low coefficient of friction and bacterial repellency, in particular at low pH values. Therefore, a kit is provided which comprises the intermittent catheter as described herein, and a catheter package. The intermittent catheter is sealed within said catheter package. A swelling liquid is also present within said catheter package and makes contact with said intermittent catheter. Said swelling liquid has a pH of 5 or less, such as 3 or less.

General Description of the Figures

FIG. 1a illustrates a route to photoinitiators of the general formula (I). A primary alcohol containing photoinitiator is first activated as an alkyl bromide, then converted to an alkyl azide. The primary amine functionalised photoinitiator is accessed via a Staudinger reduction of the alkyl azide in the presence of a suitable reducing agent, such as triphenylphosphine. The amine can be conveniently isolated as a hydrochloride salt. Subsequent reaction with either acryloyl chloride or methacryloyl chloride in the presence of a base gives the acrylamide or methacrylamide product.

FIG. 1b illustrates a route to photoinitiators of the general formula (I). A substituted azlactone can be prepared via the cyclisation of an N-acyl-α-amino acid in the presence of a suitable dehydrating agent according to known procedures. Subsequent ring-opening with an amine functionalised photoinitiator gives the acrylamide or methacrylamide product.

FIG. 1c illustrates a route to photoinitiators of the general formula (I). One way to make precursors to the photoinitiator is by the Ritter reaction; FIG. 1c, first step. In the illustrated reaction, a tertiary alcohol is exposed to strong acids to form a carbocation. This then reacts with a nitrile (acrylonitrile or methacrylonitrile).

Examples of suitable groups as alternatives to tertiary alcohols include benzylic alcohols, geminal disubstituted alkenes and trisubstituted alkenes. Primary and secondary alcohols and mono- and vicinal di-substituted alkenes can sometimes be used, but usually require harsher reaction conditions and give poorer yields. The tertiary carbocations are most stable and common choices for the Ritter reaction are formed from tertiary alcohols or geminal dialkylated alkenes. An aromatic ring adjacent to the carbocation also has a stabilizing effect and benzylic alcohols may thus be used. It is desirable that the carbocation group does not contain anything that strongly activates the aromatic ring to electrophilic attack.

After the Ritter reaction, the ring is acylated to give the final product (FIG. 1c, second step). Friedel-Crafts acylation with an acid chloride is typically used.

Synthesis of Photoinitiators—General

The photoinitiators of the general formula (I), can be synthesised via a method comprising the steps of:

a. reacting an alcohol of the general formula IIa in which Ph, Z, $R^3$ and $R^4$ are as defined herein; with an acrylonitrile of the general formula IIb in which $R^1$ is as defined as above;
in a Ritter reaction to form an acrylamide of the general formula IIc:

followed by the step of (b) reacting the acrylamide of the general formula IIc in a Friedel-Crafts acylation reaction so as to provide a photoinitiator of the general formula (I).

EXAMPLES

FIG. 1a. Synthesis of Photoinitiator-Containing Monomer

1-[p-(2-Bromoethoxy)phenyl]-2-hydroxy-2-methyl-1-propanone: 33.64 g TPP (0.15 mol) is weighed to a 1 L flask and dissolved in 120 mL dry DCM. >8 mL $Br_2$ is added slowly until a yellow colour persists. A white solid precipitates ($Ph_3PBr_2$). A little TPP is added to get back to colourless. Solution is cooled (ice) and kept under $N_2$. 2.5 mL TEA is added. 2-Hydroxy-1-[4-(2-hydroxyethoxy)phenyl]-2-methylpropan-1-one (33.64 g, 150 mmol) is dissolved in 450 mL DCM+25 mL TEA. This is then added to the cooled suspension over a period of ~1 h from an addition funnel, the ice is removed and the setup is left to heat to RT for 2 h. 5 mL AcOH is added, reaction quenched with water and mix extracted with 3×100 mL brine+(100 mL brine+$NaHCO_3$). Organic phase dried ($Na_2SO_4$), evaporated to dryness. Dried with oil pump/cold trap (~1 mBar). To get rid of most of the TPPO: Redissolved in 250 mL ether. This causes precipitation of crystals (TPPO). Cooled (freezer), filter through a cotton plug, rinse with cold ether, evaporate to dryness. $^1$H NMR (400 MHz, $CDCl_3$); 8.07 (d, J=8.8 Hz, 2H), 6.97 (d, J=8.8 Hz, 2H), 4.36 (t, J=6.2 Hz, 2H), 4.23 (s, 1H), 3.67 (t, J=6.2 Hz, 2H), 1.63 (s, 6H).

1-[p-(2-Azidoethoxy)phenyl]-2-hydroxy-2-methyl-1-propanone: 1-[p-(2-Bromoethoxy)phenyl]-2-hydroxy-2-methyl-1-propanone is dissolved in 450 mL DMF. $NaN_3$ (14.6 g, 225 mmol) is added. The mix is heated to 45° C./stirred until mostly clear solution. Heating turned off after 1 h and the reaction is left overnight at RT. DMF is removed (rotavapor 40° C., end pressure 2 mBar). 200 mL ether is added and mix is filtered, cake rinsed with 100 ml ether. Ether removed. $^1$H NMR (400 MHz, $CDCl_3$); 8.08 (d, J=8.8 Hz, 2H), 6.97 (d, J=8.8 Hz, 2H), 4.24-4.21 (m, 3H), 3.65 (t, J=4.8 Hz, 2H), 1.64 (s, 6H).

1-[p-(2-Aminoethoxy)phenyl]-2-hydroxy-2-methyl-1-propanone hydrochloride: TPP (47.2 g, 180 mmol) and all of 1-[p-(2-azidoethoxy)phenyl]-2-hydroxy-2-methyl-1-propanone are dissolved in 220 mL MeOH, and refluxed for 1 h. At the start of the reaction, a strong evolution of gas is observed ($N_2$). 20 mL water is added and refluxed for 30 min. Left at RT over weekend. MeOH and water is removed (rotavapor), redissolved in 350 mL ether (precipitation of some of the TPPO). Ether-phase filtered (cotton plug), rinsed with an additional 100 mL ether. Product precipitated with HCl(g). Most of the product precipitates as lumps on the side of the flask. The lumps in the flask are dissolved in 150 mL EtOH to a clear solution. 450 mL ether is added slowly (~1 h) with stirring. The product precipitates as small crystals. The mix is stirred for 30 m, then filtered under $N_2$, rinsed with 2×50 mL ether and dried (vacuum). Yield 22.76 g (54%). $^1$H NMR (400 MHz, $d_6$-DMSO); 8.39 (br s, 3H), 8.18 (d, J=8.7 Hz, 2H), 7.00 (d, J=8.7 Hz, 2H), 5.67 (s, 1H), 4.24 (t, J=4.8 Hz, 2H), 3.17 (t, J=4.8 Hz, 2H), 1.34 (s, 6H).

1-{2-[p-(2-Hydroxy-2-methylpropionyl)phenoxy]ethylamino}-2-propen-1-one: 1-[p-(2-aminoethoxy)phenyl]-2-hydroxy-2-methyl-1-propanone hydrochloride (15.6 g, 60 mmol) is added to a 500 mL 3-neck flask. Flask is mounted with septum and liebig condenser. The flask is heated (heating block 110° C.) and vacuum is applied for 1 h (end pressure 0.09 mBar) to dry starting material, then purged with N₂. The flask is cooled to RT and a mix of 100 mg BHT+20 mL dry TEA+300 mL DCM is added with cannula. It is stirred until clear solution. Mix is cooled with CO₂(s)/IPA and kept under N₂. 4.97 mL acryloyl chloride is added slowly (10 m) with a syringe pump. The setup is left in the cooling bath overnight. Next morning the setup is at RT. The mix is extracted with acidic saturated NaCl, then with aqueous NaCl/NaHCO₃. DCM phase dried (Na₂SO₄), filtered, evaporated to dryness. It is now an oil —when standing at RT it solidifies to a crystalline mass. 200 mL DIPE is added, refluxed for 10 min. This creates a suspension of crystals in solvent. It is then cooled in ice, pressure filtered and rinsed with 30 mL DIPE. The filtrate is returned to the flask, refluxed for 2 m, cooled and filtered. Product is dried (vacuum). Yield 11.5 g (70%). $^1$H NMR (400 MHz, CDCl₃); 7.99 (d, J=9.2 Hz, 2H), 6.86 (d, J=9.2 Hz, 2H), 6.27 (br s, 1H), 6.24 (dd, J=16.8 and 1.2 Hz, 1H), 6.07 (dd, J=16.8 and 10.4 Hz, 1H), 5.60 (dd, J=10.4 and 1.2 Hz, 1H), 4.08 (t, J=5.2 Hz, 2H), 3.72-3.68 (m, 2H), 1.55 (s, 6H).

FIG. 1b. Synthesis

1-[4-(2-Aminoethoxy)phenyl]-2-hydroxy-2-methylpropan-1-one: Triphenylphosphine (8.69 g, 33.1 mmol) is added to a solution of 1-[4-(2-azidoethoxy)phenyl]-2-hydroxy-2-methylpropan-1-one (7.50 g, 30.1 mmol) in tetrahydrofuran (120 mL) and water (12 mL) and the solution is stirred at room temperature for 18 h. Water (240 mL) is added and the mixture is acidified to pH 1 using 37% aqueous HCl solution. Impurities are extracted into ethyl acetate (3×100 mL) and the organic washes are discarded. The aqueous phase is basified to pH 14 using 20% aqueous sodium hydroxide solution, then extracted with ethyl acetate (3×150 mL). The combined organic phases are dried (Na₂SO₄) and concentrated to give the product as a clear liquid (5.70 g, 82%). A $^1$H NMR spectrum of the compound (400 MHz, CDCl₃) seems to indicate the formation of a complex mixture of oligomers in solution, nevertheless the product is used in the next step without further purification.

N-[1-({2-[4-(2-Hydroxy-2-methylpropanoyl)phenoxy]ethyl}carbamoyl)-1-methylethyl]prop-2-enamide: 1-[4-(2-Aminoethoxy)phenyl]-2-hydroxy-2-methylpropan-1-one (4.70 g, 21.1 mmol) is added to a solution of 4,4-dimethyl-2-vinyloxazol-5(4H)-one (4.90 g, 35.3 mmol) in dichloromethane (150 mL) and the solution is stirred at room temperature for 24 h. The mixture is concentrated under reduced pressure to give the crude product. Column chromatography (eluting with 20:1 dichloromethane-methanol) gives the pure product as a colourless liquid (5.01 g, 70%). $^1$H NMR (400 MHz, d₆-Acetone); 8.24 (d, J=8.6 Hz, 2H), 7.56 (br s, 1H), 7.51 (br s, 1H), 6.98 (d, J=8.6 Hz, 2H), 6.28 (dd, J=16.9 and 10.1 Hz, 1H), 6.11 (dd, J=16.9 and 1.8 Hz, 1H), 5.52 (dd, J=10.1 and 1.8 Hz, 1H), 4.74 (s, 1H), 4.13 (t, J=5.9 Hz, 2H), 3.61-3.55 (m, 2H), 1.50 (s, 6H), 1.49 (s, 6H). $^{13}$C NMR (100 MHz, d₆-Acetone); 201.88, 174.87, 164.48, 162.67, 133.11, 132.24, 127.92, 125.24, 114.13, 77.36, 66.96, 57.18, 54.67, 39.00, 24.98. ESI-MS m/z 363.2 [MH⁺].

FIG. 1c. Synthesis

N-(2-Methyl-1-phenylpropan-2-yl)prop-2-enamide: Acrylonitrile (18.0 mL, 0.260 mol) is added to a solution of 2-methyl-1-phenyl-1-propanol (35.0 g, 0.233 mol) in glacial acetic acid (125 mL) at 5-10° C. Concentrated sulfuric acid (13.6 mL, 0.260 mol) is added dropwise while maintaining the reaction temperature at <10° C. The mixture is stirred at room temperature for 16 h, then is heated at 60° C. for 6 h. The mixture is stirred at room temperature for a further 16 h then is cooled in an ice bath to <10° C. Water (300 mL) is added while maintaining the temperature at <20° C., then the resulting slurry is stirred at room temperature for 1 h. The resulting solid is collected by filtration, washed successively with water (3×100 mL) and 40-60° C. petroleum ether (3×100 mL) and is dried thoroughly under vacuum to give the pure product as a colourless solid (44.4 g, 94%). $^1$H NMR (400 MHz, CDCl₃); 7.31-7.23 (m, 3H), 7.13-7.11 (m, 2H), 6.25 (dd, J=16.8 and 1.5 Hz, 1H), 5.97 (dd, J=16.8 and 10.3 Hz, 1H), 5.58 (dd, J=10.3 and 1.5 Hz, 1H), 5.16 (br s, 1H), 3.09 (s, 2H), 1.37 (s, 6H).

Methyl {4-[2-(acryloylamino)-2-methylpropyl]phenyl}(oxo)acetate: Methyl chlorooxoacetate (16.0 mL, 0.174 mol) is added to a solution of N-(2-methyl-1-phenylpropan-2-yl)prop-2-enamide (25.0 g, 0.123 mol) in dichloromethane (200 mL) at 5-10° C. Aluminium chloride (41.0 g, 0.308 mol) is added portion-wise over 30 minutes and the resulting red solution is stirred at room temperature for 20 h. The resulting heterogeneous slurry is poured into ice water (600 mL) and the mixture is stirred for 15 minutes. Dichloromethane (500 mL) is added and organic materials are extracted into dichloromethane. Combined organic phases are washed with saturated aqueous sodium bicarbonate solution (300 mL), dried (Na₂SO₄) and concentrated to give the crude product. Recrystallization from tert-butyl methyl ether: hexane gives the pure product as a colourless solid (15.1 g, 42%). $^1$H NMR (400 MHz, CDCl₃); 7.91 (d, J=8.3 Hz, 2H), 7.26 (d, J=8.3 Hz, 2H), 6.27 (dd, J=16.8 and 1.5 Hz, 1H), 6.00 (dd, J=16.8 and 10.3 Hz, 1H), 5.62 (dd, J=10.3 and 1.3 Hz, 1H), 5.21 (br s, 1H), 3.97 (s, 3H), 3.24 (s, 2H), 1.37 (s, 6H). $^{13}$C NMR (100 MHz, CDCl$_3$); 186.07, 165.62, 164.69, 146.86, 131.87, 131.63, 130.95, 130.10, 126.90, 54.55, 53.11, 44.48, 27.90.

Ethyl {4-[2-(acryloylamino)-2-methylpropyl]phenyl} (oxo)acetate: Ethyl chlorooxoacetate (7.80 mL, 69.7 mmol) is added to a solution of N-(2-methyl-1-phenylpropan-2-yl) prop-2-enamide (10.0 g, 49.8 mmol) in dichloromethane (70 mL) at 5-10° C. Aluminium chloride (16.6 g, 145 mmol) is added portion-wise over 30 minutes and the resulting red solution is stirred at room temperature for 20 h. The heterogeneous slurry is cooled in an ice bath to <10° C. and acetonitrile (20 mL) is added dropwise while maintaining the temperature at <20° C. The resulting homogeneous solution is then poured into ice water (350 mL) and the mixture is stirred for 15 minutes. Dichloromethane (300 mL) is added and organic materials are extracted into dichloromethane. Combined organic phases are washed with saturated aqueous sodium bicarbonate solution (200 mL), dried (Na$_2$SO$_4$) and concentrated to give the crude product. Recrystallization from tert-butyl methyl ether:hexane gives the pure product as a colourless solid (6.30 g, 42%). $^1$H NMR (400 MHz, CDCl$_3$); 7.90 (d, J=8.2 Hz, 2H), 7.26 (d, J=8.2 Hz, 2H), 6.27 (dd, J=16.8 and 1.4 Hz, 1H), 5.99 (dd, J=16.8 and 10.2 Hz, 1H), 5.62 (dd, J=10.2 and 1.4 Hz, 1H), 5.20 (br s, 1H), 4.43 (q, J=7.2 Hz, 2H), 3.24 (s, 2H), 1.42 (t, J=7.2 Hz, 3H), 1.37 (s, 6H).

Abbreviations used: TPP: triphenyl phosphine, DIPE: diisopropyl ether, DCM:dichloromethane, BHT: butylated hydroxytoluene, IPA: isopropanol, TEA: triethyl amine, DMSO: dimethylsulfoxide, EtOH: ethanol, TPPO: triphenylphosphine oxide, DMF: dimethylformamide, MeOH: methanol, AcOH: acetic acid. Irgacure-acrylamide, ICAA: 1-{2-[p-(2-Hydroxy-2-methylpropionyl) phenoxy]ethylamino}-2-propen-1-one
Initiator: 2,2'-Azobis(2-methylpropionamidine) dihydrochloride
PEG35k: polyethylene glycol, molecular weight 35000
PEG2k: polyethylene glycol, molecular weight 2000
TPU-PI-10: a polyurethane copolymer from HMDI (4,4'-Diisocyanato-methylenedicyclohexane)+PEG+Speedcure 9001 (10% wt), a multifunctional polymeric photoinitiator described in Example 1 of WO2012062332.
TMPTMA: trimethylolpropane trimethacrylate
Na-AMPS: 2-Acrylamido-2-methylpropane sulfonic acid sodium salt
ACMO: 4-acryloyl morpholine Example 1, an Acrylic Acid Coating (without Sulfonate-Containing Monomer)

Synthesis of poly(acrylic-acid-co-PI) 99.6:0.4 mol %: 14.77 g acrylic acid+0.228 g ICAA+13.5 g ethanol+31.5 g water is weighed to a brown 100 mL round bottom flask. 0.279 g initiator is added, the flask is mounted with an overhead stirrer and nitrogen purge and cooled with ice. Nitrogen is purged through the system for 15 minutes. It is then sealed and kept under N$_2$ with an oil bubbler. The mix is heated to 62° C. overnight and then to 80° C. for 4 hours. A viscous solution of 25% wt poly(acrylic acid-co-ICAA) (99.6:0.4 mol %) in 30% aqueous ethanol is obtained.

Topcoat: 5.4 g of the acrylate solution synthesized above+ 0.45 g PEG35k+3.77 g water+5.39 g ethanol is weighed into a 20 mL brown screw cap vial and stirred until a clear homogeneous solution is obtained.

Primer: 5 g TMPTMA+2 g TPU-PI-10+93 g dimethyl carbonate is heated/stirred until a clear solution is obtained.
Coating Procedure Primer:
Substrate (24×24×1 mm squares made from Estane polyurethane) is treated with plasma (3 mBar air, 800W, 15 seconds) and used within 24 hours.

The substrate in mounted in the spincoater. Program is started (2000 rpm, 15 sec). As soon as sample is up to speed, a brief burst of primer is applied.

Coating procedure topcoat: The primer coated substrate is mounted in the spincoater. A drop of topcoat is placed on top and the program (1800 rpm/15 sec+2400 rpm/5 sec) is started immediately after. The coated sample is dried in an oven for 10 minutes/100° C.

UV-curing: Sample is placed on a hot-plate at 140° C. for 1 minute, and then irradiated with UV, 5 J/cm2 at 60-70° C.

The samples are immersed in water overnight. These coatings (without AMPS) are cohesive but do not swell and are not at all slippery. Even when wet, the friction against skin is much higher than the base material.

Example 2, a Poly(Na-AMPS-Co-Acrylic Acid) Based Coating

Synthesis poly(Na-AMPS-co-acrylic acid-co-ICAA) 40:59:1, 167.3 g 50% aqueous Na-AMPS+38.8 g acrylic acid+2.53 g ICAA+150 g ethanol+141.3 g water is weighed to a 1 L flask. 1.24 g initiator is added, the flask is mounted with an overhead stirrer and nitrogen purge and cooled with ice. Nitrogen is purged through the system for 15 minutes. It is then sealed and kept under N$_2$ with an oil bubbler. The mix is heated to 62° C. overnight and then to 80° C. for 4 hours. A viscous solution of 25% wt poly(Na-AMPS-co-acrylic acid-co-ICAA) (40:59:1 mol %) in 40% aqueous ethanol is obtained.
Topcoat:
29.4 g acrylate solution (poly(Na-AMPS-co-acrylic acid-co-ICAA) as synthesized above in Example 1)+8.75 g PEG2k+1.4 g PEG35k+5.30 g water+5.16 g ethanol is stirred until a homogeneous solution is obtained.

This topcoat is then spin-coated onto primer coated samples and UV-cured as described in example 1.

Samples are immersed in water overnight. The coating is firm, cohesive and have a low friction when tested wet against skin.

Example 3, Catheters Coated with a Poly(Na-AMPS-Co-Acrylic Acid) Based Coating pH4 Buffer: 10 mM formic acid, 5 mM citric acid, 0.9% NaCl, pH adjusted to 4 with 1M NaOH
Primer: TMPTMA+TPU-PI-10+dimethylcarbonate
Topcoat: 120 g acrylate solution as in example 2+36 g PEG2k+6 g PEG35k+176 g water+152 g ethanol is stirred until all is dissolved. Viscosity is now 80 mPa·s at 23° C.

Uncoated Estane catheters are treated with plasma (3 mBar air, 800 W, 15 sec). They are then dipped in primer and dried in an oven at 130° C. for 30 sec. Then they are dipped in topcoat. They are air-dried for 1 minute and then in an oven at 130° C. for 200 sec. They are then irradiated with 1 J/cm2 UV at 75° C. When immersed in water, the coating feels firm, cohesive and slippery.

The catheters are packaged in pH4 buffer and some are sterilized (β, 2×40 kGy). Catheters are removed from the buffer and friction coefficient against polished stainless steel is measured at 0 and 5 minutes on both sterilized and unsterilized samples:

| | Friction coefficient | |
|---|---|---|
| | 0 min | 5 min |
| −β | 0.0215 | 0.0209 |
| +β | 0.0273 | 0.0238 |

We can see that the friction is very low and that the catheters retain the low friction for 5 minutes after being removed from the buffer.

Example 4: A Poly(ACMO-Co-ICAA) Based Coating 13.3 mL ACMO+0.123 g ICAA+11.25 g ethanol+33.75 g water is weighed to a 100 mL flask. 0.106 g initiator is added, the flask is mounted with an overhead stirrer and nitrogen purge and cooled with ice. Nitrogen is purged through the system for 15 minutes. It is then sealed and kept under N2 with an oil bubbler. The mix is heated to 62° C. overnight and then to 80° C. for 4 hours. A viscous solution of 25% wt poly(ACMO-co-ICAA) (99.2:0.8 mol %) in 25% aqueous ethanol is obtained.

Topcoat and coating: 9 g acrylate solution as synthesized above+2.25 g 1,2-propylene carbonate+3.75 g ethanol is stirred until a homogeneous solution is obtained. This topcoat is then spin-coated onto primer coated samples and UV-cured as described in example 1. Sample is immersed in water overnight and has a lowered friction when tested wet against skin compared to the base material.

Example 5, A Poly(Na-AMPS-Co-ICAA) Based Coating 35.2 g 50% aqueous Na-AMPS+0.391 g ICAA+5.4 g ethanol+31.0 g water is weighed to a 100 mL flask. 0.106 g initiator is added, the flask is mounted with an overhead stirrer and nitrogen purge and cooled with ice. Nitrogen is purged through the system for 15 minutes. It is then sealed and kept under N2 with an oil bubbler. The mix is heated to 62° C. overnight and then to 80° C. for 4 hours. A viscous solution of 25% wt poly(Na-AMPS-co-ICAA) (98.2:1.8 mol %) in 10% aqueous ethanol is obtained.

Topcoat and coating: 7.56 g acrylate solution as synthesized above+1.89 g glycerol+2.75 g water+2.80 g ethanol is stirred until a homogeneous solution is obtained. This topcoat is then spin-coated onto primer coated samples and UV-cured as described in example 1.

Samples are immersed in water overnight. They are firm, cohesive and have a low friction when tested wet against skin.

Example 6

Speedicath Control Samples

Topcoat: 24 g PVP K90+40 g citrofol A1+20 g N-methylpyrrolidone+0.12 g esacure KIP 150+116 g ethanol is stirred until all components are dissolved.

This solution is coated onto plasma treated estane squares as in example 1. The samples are dried in an oven at 100° C. for 10 minutes. They are placed in an aluminium tray on a hotplate 140° C./1 minute. The tray is then placed on the conveyer belt of a Fusion UV-tunnel, I6P1 (Fusion UV Systems Inc.) at 40% intensity and 2.7 m/s. When cooled, a sample is immersed in water overnight. The coating is firm, cohesive and slippery.

Repellency

Plates coated as in example 2 are immersed in buffer as in example 3 at pH 3 overnight. They are compared to a SpeediCath coating (control). This coating is immersed in PVP-liquid (6% wt PVP k-15, 0.9% wt NaCl).

Repellent CFU Catheter 2.0 Test (a Modified Version of ISO22196)

Unsterile square samples and controls are placed in 70% EtOH for 20 minutes on a shaking table. Next the samples are washed once in sterile swelling media, and then placed in sterile swelling media O/N at RT.

E. Coli are transferred to an agar plate 2 days before use. 1 day before use, one colony is transferred to growth medium and placed in a shaking cabinet at 35° C. The bacteria are washed 1 time in 0.9% NaCl and resuspended in 0.9% NaCl. The inoculum concentration should be between $1 \times 10^7$-$2.5 \times 10^7$ CFU/mL.

The square samples with coating are transferred to a sterile petri dish with the coating side up. 150 μL of the bacterial solution is applied to the coating. A coverfilm is placed on top of the bacterial solution to ensure that the bacterial solution covers the entire sample and to avoid drying of the coating under test. Contact time is 5 minutes. Samples are washed 3×1 min in 100 ml 0.9% NaCl on a shaking table. Then, the samples are transferred to a tube containing 3 ml of sterile 0.9% NaCl. The samples are positioned so that the coating is in contact with the liquid. Next, the samples are treated in a degas bath for 5 minutes and ultrasound treated for 5 minutes to release the attached bacteria from the surface. 100 μL is spread-plated to a LB agar plate, in duplicate, and placed at 35° C. O/N. CFU is counted after 24 hours.

The test results are measured as CFU number and Log 10 to CFU.

The results can be used to study the repellent effect on a coated square samples compared to a control. The reporting of the repellent effect compared to the control is provided as a percentage in Table 1. It can be seen that the coatings of the examples provide improved bacterial repellence.

TABLE 1

| Repellent CFU assay, *P. Aeruginosa*, n = 6, inoculum 1.41 × 10⁷ | |
|---|---|
| | Coating (as Example 2) pH 3 |
| Percent attachment of CFUs (control = 100) | 30 |

EMBODIMENTS

The following numbered embodiments are provided:

Embodiment 1

A polymeric coating for a urinary catheter, being a copolymer of at least a first photoinitiator monomer and at least one second monomer;
said first monomer having formula (I):

(I)

in which:
Pi is a photoinitiator moiety;
Z is a linker moiety selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$—, optionally substituted —[NHR$^1$—($C_1$-$C_{12}$ alkylene)]$_n$-; optionally substituted —[S—($C_1$-$C_{12}$ alkylene)]$_n$—; and combinations thereof; wherein n is an integer from 1-20, and wherein R$^a$ is H or optionally substituted $C_1$-$C_6$ alkyl;
R$^1$ is selected from H and optionally substituted $C_1$-$C_6$ alkyl;
R$^2$ is selected from H and optionally substituted $C_1$-$C_6$ alkyl;
wherein R$^2$ or a part thereof may be linked to Z to form one or more ring structures;
and wherein said at least one second monomer comprises an unsaturated C=C bond.

Embodiment 2

The polymeric coating according to embodiment 1, wherein linker Z in formula (I) has the structure:

in which the —C(R$^3$)(R$^4$)— moiety is linked to the acrylamide N-atom in formula (I);
wherein Za is a linker moiety selected from a single bond, optionally substituted $C_1$-$C_{12}$ alkylene, optionally substituted $C_1$-$C_{12}$ alkenylene; —O—; —S—; —NR$^a$—; —CO—NR$^a$—; optionally substituted heterocyclyl; optionally substituted arylene; optionally substituted —[O—($C_1$-$C_{12}$ alkylene)]$_n$—, optionally substituted —[NHR$^1$—($C_1$-$C_{12}$ alkylene)]$_n$; optionally substituted —[S—($C_1$-$C_{12}$ alkylene)]$_n$-; and combinations thereof; wherein n is an integer from 1-20, and wherein R$^a$ is H or optionally substituted $C_1$-$C_6$ alkyl;
R$^3$ and R$^4$ are independently selected from H and optionally substituted $C_1$-$C_6$ alkyl; wherein R$^3$ or R$^4$, or a part thereof, may be linked to Za to form one or more ring structures.

Embodiment 3

The polymeric coating according to embodiment 2, wherein R$^3$ and R$^4$ in formula (I) are independently selected from optionally substituted $C_1$-$C_6$ alkyl, $C_1$-$C_6$ alkyl, methyl, ethyl, and propyl.

Embodiment 4

The polymeric coating according to any one of embodiments 2-3, wherein R$^3$ and R$^4$ in formula (I) are the same.

Embodiment 5

The polymeric coating according to any one of the preceding embodiments, wherein Z in formula (I) is selected from a single bond, $C_1$-$C_{12}$ alkylene, $C_1$-$C_{12}$ alkenylene; —O—; —S—; —NR$^a$—; and —[O—($C_1$-$C_{12}$ alkylene)]$_n$—, wherein R$^a$ is H or optionally substituted $C_1$-$C_{12}$ alkyl and n is an integer from 1-20.

Embodiment 6

The polymeric coating according to any one of the preceding embodiments, wherein Z in formula (I) is selected from a single bond, $C_1$-$C_{12}$ alkylene or —O—($C_1$-$C_{12}$ alkylene)-, $C_1$-$C_6$ alkylene, and —O—($C_1$-$C_6$ alkylene)—.

Embodiment 7

The polymeric coating according to any one of embodiments 2-4, wherein Za in formula (I) is selected from a single bond, $C_1$-$C_{12}$ alkylene, $C_1$-$C_{12}$ alkenylene; —O—; —S—; —NR$^a$—; and —[O—($C_1$-$C_{12}$ alkylene)]$_n$—, wherein R$^a$ is H or optionally substituted $C_1$-$C_{12}$ alkyl and n is an integer from 1-20.

Embodiment 8

The polymeric coating according to embodiment 7, wherein Za in formula (I) is selected from a single bond, $C_1$-$C_{12}$ alkylene, —O—($C_1$-$C_{12}$ alkylene)-, $C_1$-$C_6$ alkylene, and —O—($C_1$-$C_6$ alkylene)-.

Embodiment 9

The polymeric coating according to any one of the preceding embodiments, in which R$^1$ in formula (I) is H or methyl.

Embodiment 10

The polymeric coating according to any one of the preceding embodiments, wherein Pi in formula (I) is a Norrish type-I photoinitiator moiety.

Embodiment 11

The polymeric coating according to any one of the preceding embodiments, wherein Pi in formula (I) is selected from the group consisting of: benzoin ethers, 1-phenyl-2-hydroxy-2-alkyl ketones, 1-phenyl-2-amino-2-alkyl ketones, dibenzosuberones, benzils, benzil ketals, acetophenones, α-alkoxy-acetophenones, α,α-dialkoxy-acetophenones, α-hydroxy-α-alkyl-phenones, α-hydroxy-α, α-dialkyl-phenones, alkyl phenylglyoxylates, camphorquinones, acyl-phosphine oxides, and phenyl ketocoumarins.

Embodiment 12

The polymeric coating according to any one of the preceding embodiments, wherein Pi in formula (I) is a photoinitiator moiety selected from the group consisting of: acetophenones, α-alkoxy-acetophenones, α,α-dialkoxy-ac- etophenones, α-hydroxy-α-alkyl-phenones, α-hydroxy-α,α-dialkyl-phenones, and alkyl phenylglyoxylates.

Embodiment 13

The polymeric coating according to any one of the preceding embodiments, wherein Pi in formula (I) is a Norrish Type-I photoinitiator moiety having the general formula (V):

-Ph-(X)$_m$      (V)

wherein Ph is an optionally-substituted phenyl ring;
wherein m is an integer of 1-5, such that m X moieties may be present at any position on Ph;
and wherein X is selected from in which R is selected from H or optionally substituted $C_1$-$C_6$ alkyl.

Embodiment 14

The polymeric coating according to embodiment 13, wherein said X is present at the para-position on Ph.

Embodiment 15

The polymeric coating according to any one of embodiments 13-14, wherein m is 1 or 2, preferably 1.

Embodiment 16

The polymeric coating according to any one of embodiments 1-15, in which the monomer of formula (I) has the general formula (Ia):

wherein $R^1$, $R^2$, $R^3$, Z, X, and m are as defined in any one of embodiments 1-15.

Embodiment 17

The polymeric coating according to any one of embodiments 1-16, in which the monomer of formula (I) has the general formula (Ib):

wherein Za is a linker moiety selected from a single bond, —$C_1$-$C_6$ alkylene-, and —O—($C_1$-$C_6$ alkylene)—;
$R^1$ and $R^2$ are as defined in any one of the preceding embodiments;
$R^3$ and $R^4$ are independently selected from H and methyl;
X is selected from

Embodiment 18

A polymeric coating according to any one of embodiments 1-17, in which the monomer of formula (I) is selected from:

-continued

-continued

-continued

Embodiment 19

The polymeric coating according to embodiment 1, wherein said at least one second monomer comprises an acryloyl moiety.

Embodiment 20

The polymeric coating according to any of the preceding embodiments, wherein said second monomer is selected from acrylic acid, an acrylamide or an acrylic acid ester, and mixtures thereof.

Embodiment 21

The polymeric coating according to any of the preceding embodiments, wherein said second monomer is selected from acrylic acid, C1-C6 acrylic esters, 2-acrylamido-2-methylpropane sulfonic acid, 2-acrylamido-2-methylpropane sulfonic acid sodium salt, 4-acryloyl-morpholine, hydroxyethyl methacrylate, acrylamide, N,N-dimethylacrylamide, methyl vinyl ether, ethyl vinyl ether, and mixtures thereof.

Embodiment 22

The polymeric coating according to any of the preceding embodiments, wherein said polymeric coating comprises two second monomers, which are copolymerised together with the first photoinitiator monomer.

Embodiment 23

The polymeric coating according to embodiment 22, wherein the two second monomers are acrylic acid and sodium 2-acrylamido-2-methylpropane sulfonic acid (Na-AMPS).

Embodiment 24

The polymeric coating according to any of the preceding embodiments, said coating additionally comprising a plasticiser.

Embodiment 25

A method for synthesizing a polymeric coating according to any one of the preceding embodiments, said method comprising the step of co-polymerizing a first monomer of formula (I) with at least one second monomer comprising an unsaturated C=C bond.

Embodiment 26

A method for coating a urinary catheter, said method comprising the steps of:
a. applying the polymeric coating of any one of embodiments 1-24 to an outer surface of said urinary catheter and
b. irradiating said polymer coating so as to fix the polymeric coating to said outer surface.

Embodiment 27

The method according to embodiment 26, wherein said urinary catheter comprises a substrate material and a primer layer, and wherein the primer layer constitutes the outer surface of the urinary catheter.

Embodiment 28

The method according to embodiment 27, wherein said primer layer is a layer of polyurethane polymer.

Embodiment 29

The use of the polymeric coating according to any one of embodiments 1-24 for providing bacteria repellency to a surface of a urinary catheter.

Embodiment 30

An intermittent urinary catheter coated with the polymeric coating according to any one of embodiments 1-24.

Embodiment 31

A kit comprising the intermittent catheter according to embodiment 30, and a catheter package, wherein said intermittent catheter is sealed within said catheter package, and wherein a swelling liquid is also present within said catheter package and in contact with said intermittent catheter, wherein said swelling liquid has a pH of 5 or less, such as 4 or less.

Although the technology has been described with reference to a number of examples and reaction schemes, it should not be considered as limited by the above description. The full scope of the technology is defined by the appended claims.

The invention claimed is:
1. A polymeric coating comprising: a copolymer of at least a first photoinitiator monomer and a second monomer, wherein the first photoinitiator monomer is of formula (I):

wherein Pi comprises a photoinitiator moiety having the formula (V):

-Ph-(X)$_m$ (V)

wherein Ph comprises an optionally-substituted phenyl ring:
wherein m is an integer of 1-5, such that m X moieties may be present at any position on Ph; and
wherein X is selected from:

or wherein each R is a H or an optionally substituted $C_1$-$C_6$ alkyl;

—C(R$^3$)(R$^4$)—Za— wherein the —C(R$^3$)(R$^4$)— moiety is linked to the acrylamide N-atom in formula (1);
wherein Za is selected from a single bond, an optionally substituted $C_1$-$C_{12}$ alkylene, or an optionally substituted [—O—($C_1$-$C_{12}$ alkylene)—]$_n$, wherein n is an integer from 1-20;
R$^3$ and R$^4$ are each independently an optionally substituted C1-C6 alkyl;
$R_1$ is H or an optionally substituted $C_1$-$C_6$ alkyl;
$R_2$ is H; and
wherein the second monomer comprises an unsaturated C=C bond.

2. The polymeric coating according to claim 1, wherein R$^3$ and R$^4$ in formula (I) are selected from the group consisting of optionally substituted $C_1$-$C_6$ alkyl, $C_1$-$C_6$ alkyl, methyl, ethyl, and propyl.

3. The polymeric coating according to claim 1, wherein R$^3$ and R$^4$ in formula (I) are the same.

4. The polymeric coating according to claim 1, in which R$^1$ in formula (I) is selected from H or methyl.

5. The polymeric coating according to claim 1, wherein the X is present at the para-position on Ph.

6. The polymeric coating according to claim 1, wherein m is 1 or 2.

7. A polymeric coating according to claim 1, wherein the first photoinitiator monomer is selected from the group consisting of:

and mixtures thereof.

8. The polymeric coating according to claim 1, wherein the second monomer comprises an acryloyl moiety.

9. The polymeric coating according to claim 1, wherein the second monomer is selected from the group consisting of acrylic acid, an acrylamide, an acrylic acid ester and mixtures thereof.

10. The polymeric coating according to claim 1, wherein the second monomer is selected from the group consisting of acrylic acid, $C_1$-$C_6$ acrylic esters, 2-acrylamido-2-methylpropane sulfonic acid, 2-acrylamido-2-methylpropane sulfonic acid sodium salt, 4-acryloyl-morpholine, hydroxyethyl methacrylate, acrylamide, N,N-dimethyl-acrylamide, methyl vinyl ether, ethyl vinyl ether, and mixtures thereof.

11. The polymeric coating according to claim 1, wherein the polymeric coating comprises two second monomers, which are copolymerised together with the first photoinitiator monomer.

12. The polymeric coating according to claim 1, the coating further comprising a plasticizer.

\* \* \* \* \*